US009220484B2

United States Patent
Krueger

(10) Patent No.: US 9,220,484 B2
(45) Date of Patent: Dec. 29, 2015

(54) REDUCED PROFILE BIOPSY DEVICE

(71) Applicant: CareFusion 2200, Inc., San Diego, CA (US)

(72) Inventor: John A. Krueger, Muskego, WI (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 13/690,730

(22) Filed: Nov. 30, 2012

(65) Prior Publication Data

US 2013/0090570 A1   Apr. 11, 2013

Related U.S. Application Data

(63) Continuation of application No. 12/827,660, filed on Jun. 30, 2010, now Pat. No. 8,343,070.

(51) Int. Cl.
*A61B 10/00* (2006.01)
*A61B 10/02* (2006.01)
*A61B 17/00* (2006.01)
*A61B 19/00* (2006.01)

(52) U.S. Cl.
CPC ..... *A61B 10/0275* (2013.01); *A61B 2010/0093* (2013.01); *A61B 2010/0208* (2013.01); *A61B 2017/00367* (2013.01); *A61B 2019/462* (2013.01)

(58) Field of Classification Search
CPC ..... A61B 2010/0208; A61B 10/0233–10/0275
USPC ........................................... 600/564–568, 562
See application file for complete search history.

(56) References Cited

U.S. PATENT DOCUMENTS

| 5,951,489 | A | 9/1999 | Bauer |
| 5,993,399 | A * | 11/1999 | Pruitt et al. .................. 600/562 |
| 6,120,463 | A | 9/2000 | Bauer |
| 6,749,576 | B2 | 6/2004 | Bauer |
| 7,585,282 | B2 * | 9/2009 | Hancock ..................... 600/567 |
| 7,651,467 | B2 | 1/2010 | Lubock et al. |
| 2004/0034280 | A1 | 2/2004 | Privitera et al. |
| 2004/0097832 | A1 | 5/2004 | Adams et al. |
| 2005/0203440 | A1 | 9/2005 | Gellman et al. |
| 2009/0299221 | A1 | 12/2009 | Bacon et al. |

* cited by examiner

*Primary Examiner* — Brian Szmal
*Assistant Examiner* — H. Q. Nguyen
(74) *Attorney, Agent, or Firm* — Arent Fox LLP

(57) ABSTRACT

A biopsy device is disclosed that includes a housing maintaining a stylet and a cannula, a control device operable to actuate the stylet and the cannula with respect to the housing and a removable handle coupleable to the control device to load the stylet and the cannula, wherein the handle is configured to modify the device from to a loading configuration a delivery configuration such that the device has a reduced profile for obtaining a tissue sample.

20 Claims, 6 Drawing Sheets

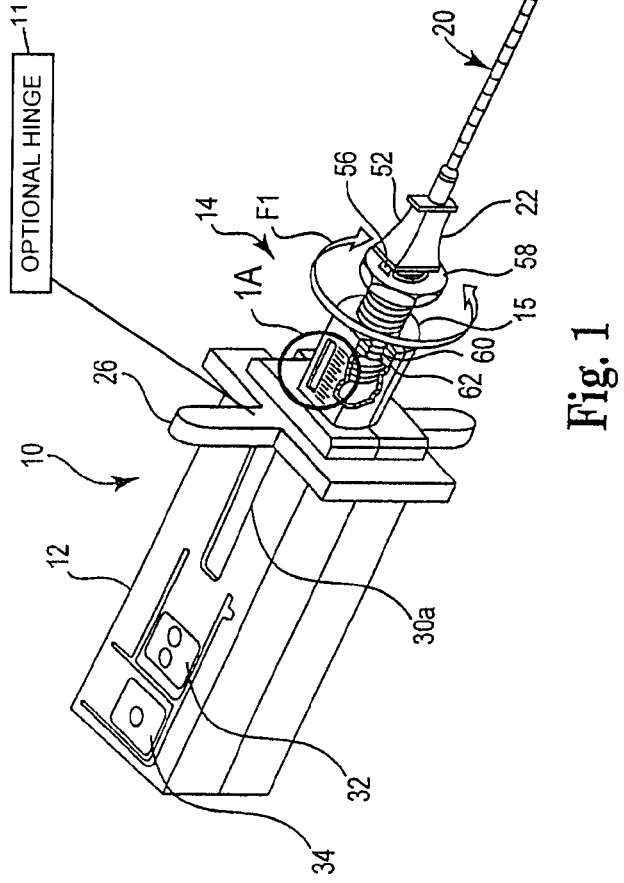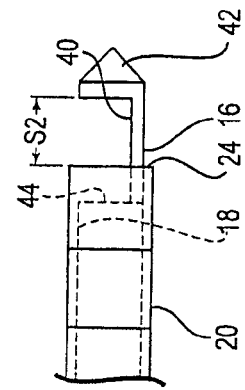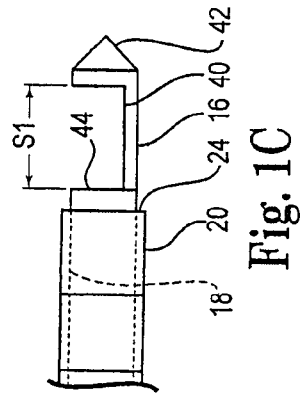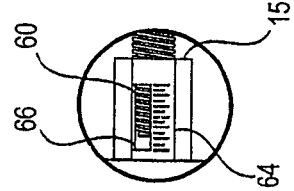

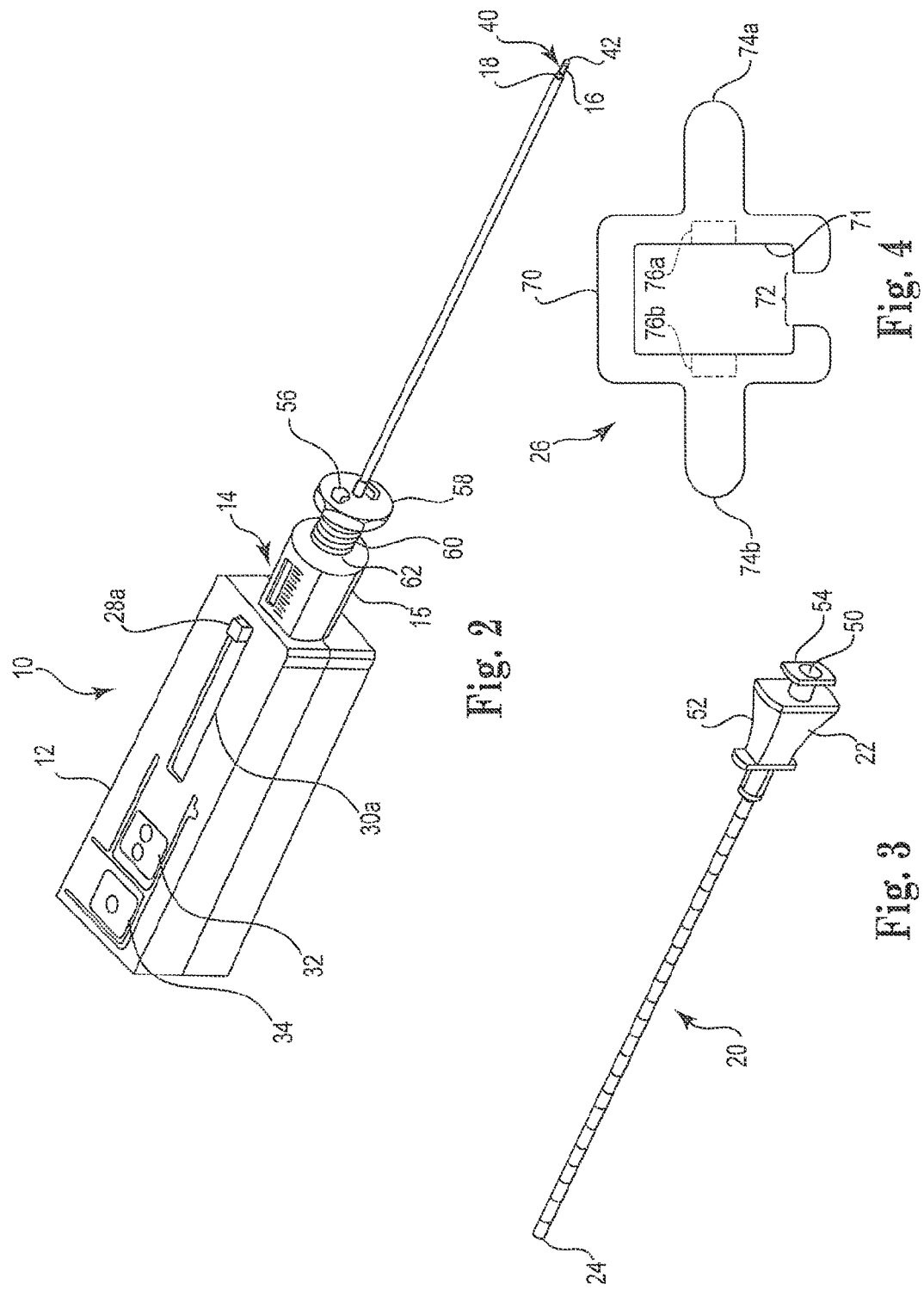

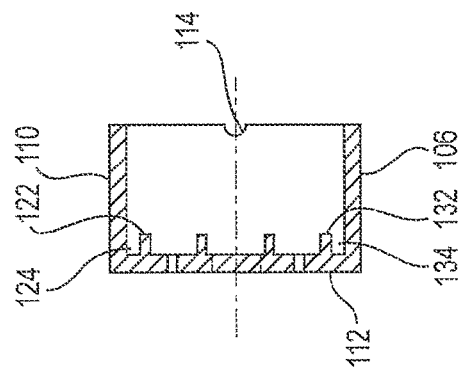
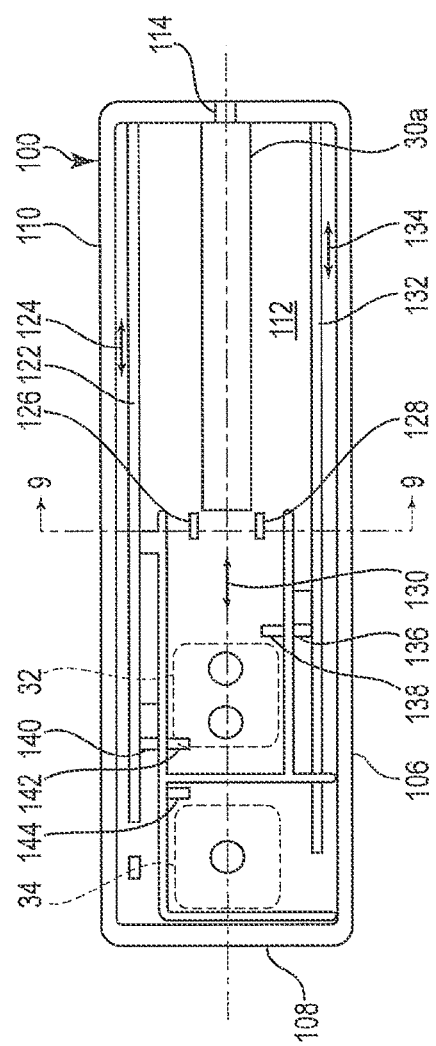

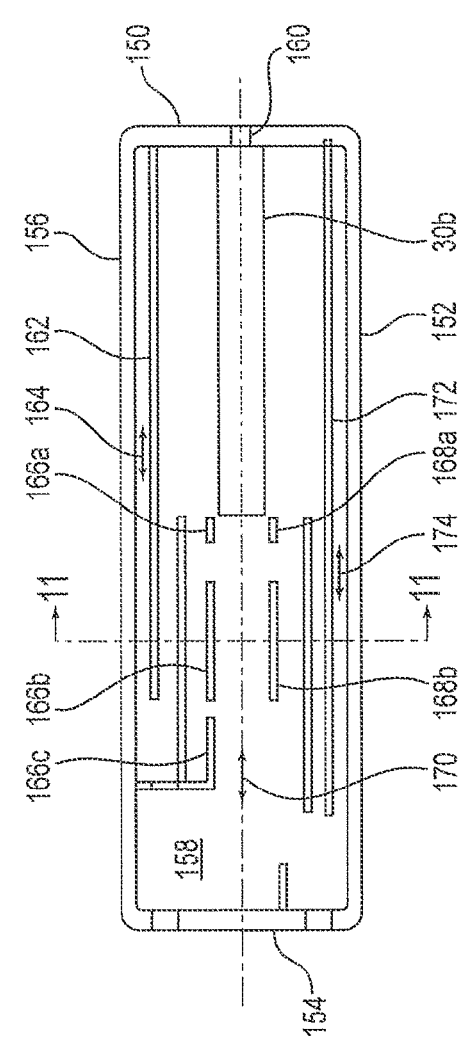

REDUCED PROFILE BIOPSY DEVICE

RELATED APPLICATIONS

This application is a continuation of co-pending U.S. patent application Ser. No. 12/827,660, filed on Jun. 30, 2010 entitled "Reduced Profile Biopsy Device," by Krueger et al., and assigned to the assignee of the present application.

TECHNICAL FIELD

The present disclosure relates to a device for tissue removal in biopsy procedures. In particular, the disclosure relates to a reduced profile biopsy device.

BACKGROUND

Biopsy needle devices with handpieces containing an actuating apparatus which activates the motion of a biopsy needle are known. For example, U.S. Pat. No. 4,958,625 to Bates et al. discloses a biopsy device containing a handpiece and stylet which projects independently of a cannula and wherein the handpiece contains an attachment means for the cannula. The insertion guide used in such systems includes a cannula guide made up of a hollow small tube in which the proximal end bears a trigger, and is equipped with an attachment means, as well as a luer lock for a syringe to introduce a medicament to the site after tissue removal.

Procedures using actuated biopsy needles typically involve first inserting the biopsy needle and cannula insertion guide into the patient's body by positioning the distal end of the needle in proximity to the object to be sampled. Upon determining the desired position (e.g., by ultrasound, magnetic resonance (CAT scan) or other technique), a stylet and cannula cutting edge are sequentially activated to obtain the sample. Once the sampling step has been performed, the attachment means are released and the biopsy needle withdrawn from the cannula insertion guide to check the sample. If the sample is incorrect or otherwise insufficient, a new biopsy needle is inserted into the cannula insertion guide and the sampling sequence is repeated. After obtaining the desired sample, a medicament can be administered to the site by applying a syringe to the insertion guide.

Current biopsy devices include wings extending from the handpiece to allow a user to grasp and/or load the actuating apparatus. While the wings are useful in loading the actuating apparatus, extension of the wings from the handpiece can interfere with an approach position of the biopsy device with respect to the tissue of interest. In particular, the wings can interfere with a desired angle of approach for the biopsy device, thus preventing a user from obtaining a desired sample in relation to a mass.

SUMMARY

Concepts presented herein relate to a reduced profile biopsy device enabling approach of the biopsy device relative to a tissue site at a greater range of angles. In one aspect, the concepts relate to a biopsy device having a housing maintaining a stylet and a cannula. A control device is operable to actuate the stylet and the cannula with respect to the housing. A handle is coupleable to the control device to load the stylet and the cannula. The handle is configured to modify the device from a loading configuration to a delivery configuration such that the device has a reduced profile for obtaining a tissue sample.

In another aspect, a method of operating a biopsy device having a biopsy needle assembly comprising a stylet and cannula is disclosed. The method includes loading the cannula and stylet, reducing a profile of the biopsy device and operating the biopsy device to obtain a sample.

In yet a further aspect, a biopsy device includes a housing maintaining a stylet and cannula. The housing includes upper and lower slots. A control device is operable to actuate the stylet and the cannula. The control device includes upper and lower tabs extending through the upper and lower slots of the housing, respectively. A removable handle includes an inner perimeter shaped to be positioned around the housing and a body configured to engage the upper and lower tabs of the control device. First and second wings extend from the body and are shaped to be grasped by a user to load the stylet and cannula when the body engages the upper and lower tabs of the control device.

BRIEF DESCRIPTION OF THE DRAWINGS

FIG. 1 is an overall perspective view of one embodiment of a biopsy device.

FIG. 1A is a detailed view of one embodiment of a longitudinal adjustment element of the device having an indicating element.

FIG. 1B is a detailed view of one embodiment of distal portions of the biopsy needle assembly of the device.

FIGS. 1C and 1D together schematically depict adjustment of the biopsy needle assembly of the device relative to the cannula insertion guide, which will produce different sample sizes after adjustment of the device.

FIG. 2 is a perspective view of one embodiment of the device without a cannula insertion guide and handle attached thereto.

FIG. 3 is a perspective view of the cannula insertion guide portion of the device.

FIG. 4 is a plan view of a removable handle for use with the biopsy device.

FIG. 8 is a plan view of a top shell of the housing.

FIG. 9 is a sectional view of the top shell of the housing taken along the line 9-9 in FIG. 8.

FIG. 10 is a plan view of a bottom shell of the housing.

FIG. 11 is a sectional view of the bottom shell of the housing taken along the line 11-11 in FIG. 10.

DETAILED DESCRIPTION

Figure 5:
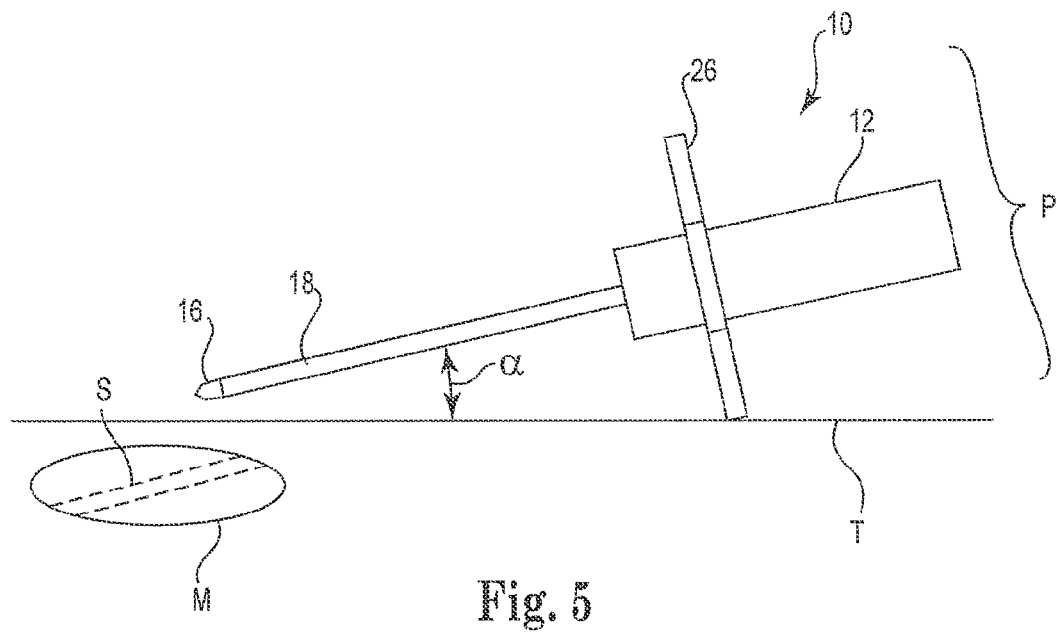
FIG. 5 is a schematic view of the biopsy device in a loading configuration in relation to a target tissue site.

As illustrated in FIGS. 1-4, biopsy device 10 includes a housing 12, a longitudinal adjusting element 14 including a body 15 coupled to the housing 12, a biopsy needle assembly including a perforating stylet 16 coaxially positioned within a cannula 18 and a cannula insertion guide 20 having a proximal portion 22 and a distal portion 24. A removable handle 26 is configured to be positioned around the housing 12 and operable to engage tabs 28a (FIGS. 2 and 7) and 28b (FIG. 7) so as to load the biopsy device 10 for collection of a sample from a patient. In particular, the handle 26 modifies a profile of the biopsy device from a first, loading configuration having an expanded profile, to a second, delivery configuration having a reduced profile. By reducing the profile of the biopsy device 10, a user can approach tissue at an expanded range of angles. As used herein, "profile" of the biopsy device 10 refers to the outermost dimensions of the device. In the particular example presented herein, handle 26 increases a height dimension of the device 10 when coupled to housing 12 (i.e., creating an increased profile), whereas removing handle 26 from housing 12 will decrease the height dimension (i.e., creating a reduced profile). As such, when in the delivery configuration, the overall profile of the device will be similar to the profile of the housing 12.

In the loading configuration, a user positions handle 26 around an outer circumference of the housing 12 to engage and actuate tabs 28a and 28b within slots 30a (FIGS. 1, 2 and 7) and 30b (FIG. 7), respectively, of the housing 12 so as to load (or wind) the stylet 16 and the cannula 18 for tissue removal. To actuate the tabs 28a and 28b, the user moves the handle 26 in a direction away from a front of the housing 12 and towards a rear of the housing 12. A first movement of tabs 28a and 28b will partially retract and load the cannula 18 into the housing 12. Once the cannula 18 is loaded, the user moves the handle 26 a second time in order to partially retract the stylet 16 into the housing 12. After the stylet 16 and cannula 18 have been retracted, handle 26 can be removed from the housing 12 to modify the configuration of the device 10 to the delivery configuration, wherein the overall profile of device 10 is reduced. As such, device 10 can be inserted with respect to the tissue of interest at a greater range of angles. Once inserted to the desired position for sampling, a user (e.g., a practitioner) can depress buttons 32 and 34 to actuate the stylet 16 and cannula 18 in immediate succession. Alternatively, button 34 can be depressed to actuate stylet 16 only, where button 32 is ultimately depressed to actuate cannula 18.

As illustrated in FIG. 1B, the stylet 16 of the device 10 contains an indentation (or groove) 40 located near a distal portion of the stylet 16 proximal to a tip 42 which permits encroachment of the tissue to be sampled when the biopsy needle portion is positioned in proximity to the tissue to be sampled. In one embodiment, the configuration of tip 42 facilitates perforation or piercing through tissue to reach the site. In FIG. 1B, the distal tip 42 of the stylet 16 is shown in an extended position with the stylet indentation 40 fully exposed beyond the cannula 18. A distal end of the cannula 18 includes a cutting edge 44 configured to facilitate cutting of tissue within indentation 40 upon actuation of the cannula 18.

The control device for operation of said biopsy needle assembly can comprise any suitable manually operated actuating mechanism adapted to co-axially, sequentially and rapidly move or displace the stylet relative to the cannula cutting edge. For example, a spring-loaded assembly with a trigger mechanism can be used. In one embodiment, a trigger mechanism as disclosed in U.S. Pat. No. 5,951,489, the contents of which are hereby incorporated in their entirety, can be used. An exemplary control device 90 is described in more detail with respect to FIGS. 7-11 below. In general, the handle 26 is coupleable to the control device through tabs 28a and 28b so as to load stylet 16 and cannula 18.

As can be seen in FIG. 3, the cannula insertion guide 20 includes a cylindrical hollow cannula 50 and is adapted for co-axial alignment and internal accommodation and placement of the biopsy needle assembly of the device. The proximal end 22 of the cannula insertion guide 20 can be of any suitable configuration or structure provided it includes a proximal attachment means. In one embodiment, the proximal attachment means of the cannula insertion guide is a removable attachment means, i.e., one which can be reversibly detached from and mechanically compatible with the corresponding attachment means positioned on the longitudinal adjusting element 14. In one embodiment and as shown in the figures, the proximal portion 22 of the cannula insertion guide 20 comprises a tang 52 and attachment means in the form of a twist lock component 54 adapted for engagement with a corresponding receiving component 56 (FIG. 2) of the distal attachment element 58 (FIG. 2) located on the longitudinal adjusting element 14 of the device.

Various attachment systems can be used to couple the cannula insertion guide to the longitudinal adjusting element provided they together enable continuity of placement for the biopsy needle assembly therethrough. Examples of suitable attachment systems include, but are not limited to, a luer lock assembly, superimposed fitting components, channel and groove, screw-type assembly, and the like. In a further embodiment, cannula insertion guide 20 can be eliminated such that an attachment system is not needed.

The longitudinal adjusting element 14 of the device 10 is positioned between the housing 12 and the proximal portion 22 of the cannula insertion guide 20 and maintains the distal attachment element 58 and a lumen (not shown) adapted for placement of the biopsy needle assembly. The longitudinal adjusting element 14 is adapted to co-axially adjust the position of the cannula insertion guide 20 relative to the biopsy needle assembly of the device. The body 15 of the longitudinal adjusting element 14 can be integral with housing 12, or, in an alternative embodiment, separately coupled thereto.

The longitudinal adjusting element 14 and can be configured in a variety of ways to accomplish the same result provided the longitudinal adjusting element 14 can be incrementally and controllably adjusted in a precise manner. In one embodiment and as shown in the figures, the longitudinal adjusting element 14 comprises a threaded element 60 adapted for engagement and rotatable movement with a threaded channel 62 located in the body 15. In other words, the longitudinal adjusting element 14 can be in the configuration of a screw-like component which adjusts the space between the cannula insertion guide 20 and the housing 12 upon rotation as shown by arrow F1 in FIG. 1. In an alternative embodiment, longitudinal adjusting element 14 can be eliminated.

In a further embodiment, the biopsy device further comprises an indicating element. The indicating element can comprise any suitable structure, indicia or combination thereof which indicates the position and longitudinal displacement of the cannula insertion guide relative to the housing in an externally viewable manner. In one embodiment, the indicating element comprises one or a series of calibrated marking(s) on the body 15 from which to reference a point located on the longitudinal adjusting element 14 of the device 10. The point located on the longitudinal adjusting element 14 can be the truncated proximal end of the element or, alternatively, a viewable indicia or marking(s) located on the longitudinal adjusting element per se.

FIG. 1A illustrates one embodiment of an indicating element. In this embodiment, externally viewable calibrated markings 64 are located on the body 15 and are located proximate to a reading window 66, which permits a viewable reference to the proximal end of the longitudinal adjusting element 14. Accordingly, the markings 64 are calibrated to correspond to and measure the distance of the exposed stylet tip 42 beyond the distal end of the cannula 50 of the insertion guide 20, the practitioner can obtain a precise length of sample in operation.

FIGS. 1C and 1D together depict the biopsy needle assembly motion relative to the cannula insertion guide after adjustment of the device. FIG. 1C illustrates a first position of the device wherein the tip of the stylet 42 and indentation 40 have been adjusted to obtain a full length sample. In this depiction, the stylet tip 42 and cannula 18 are both extended beyond the distal end 24 of the cannula 50 of the cannula insertion guide 20. When positioned within tissue and actuated, the cannula 18 stroke will sever and obtain a sample having the size depicted as S1.

FIG. 1D illustrates the positioning of the distal end 24 of the cannula insertion guide 20 relative to the biopsy needle assembly after adjustment of the longitudinal adjusting element (not shown). Rotational movement of the longitudinal adjusting element with the cannula insertion guide attached thereto (as seen in FIG. 1, for example) in a direction away from the body 15 incrementally and precisely moves the distal end 24 of the cannula insertion guide 20 over the stylet thereby reducing the exposure of the indentation on the stylet and, thus, reduces the amount of tissue which contacts the stroke of the cutting edge 16. Accordingly, after insertion and actuation of the device, a sample having a size S2 is obtained which is smaller in comparison to a sample obtained prior to longitudinal adjustment.

When used with the longitudinal adjusting element 14 and cannula insertion guide 20, the device 10 can be used in a method of obtaining a tissue sample having a predetermined size from a tissue site using a biopsy device as described herein comprising the steps of a) inserting and positioning the cannula insertion guide and biopsy needle assembly of the device in proximity to the tissue sampling site, and b) actuating the biopsy needle assembly of the device to obtain a sample, wherein the sample size is determined prior to actuating the biopsy needle assembly by adjustment of the longitudinal adjusting element of the device.

In use, the practitioner can view the indicating element such as that depicted in FIG. 1A to determine the length of the cutting stroke of the biopsy needle assembly and makes the desired adjustment prior to actuating the device and obtaining the sample. Viewing the indicating element in conjunction with adjusting of the longitudinal adjusting element of the device allows the practitioner to obtain a sample of a particular size and, if circumstances require, avoid more damage than necessary to tissues surrounding the sampling site.

Whether or not longitudinal adjusting element 14 is used to adjust a sample size, handle 26 is used to load the biopsy device 10 during a loading configuration and is subsequently removed from the biopsy device 10 in a delivery configuration. In particular, as illustrated in FIG. 4, handle 26 includes a rectangular body 70 defining an inner perimeter 71 and an opening 72. Opposed wings 74a and 74b extend outwardly from the body 70. In one embodiment, wings 74a and 74b include slightly concave surfaces to improve grasping of handle 26 by a practitioner. Additionally, opposed recesses 76a and 76b (shown in phantom) are provided on a rear surface of the handle 26 to engage tabs 28a and 28b of biopsy device 10, respectively.

To load the device 10, handle 26 is positioned around a circumference of the housing 12, where inner perimeter 71 is shaped to loosely engage the housing 12. Opening 72 allows handle 26 to be slid over the cannula 18 from the side. Once handle 26 is positioned over housing 12, recesses 76a and 76b engage tabs 28a and 28b, which extend externally from the housing 12 through slots 30a and 30b. The position of handle 26 places the biopsy device 10 in the loading configuration having an increases profile. When in the loading configuration the practitioner can easily grasp handle 26 to load device 10. In particular, due to the design of device 10, one-handed loading can be accomplished, wherein the practitioner uses a forefinger and middle finger to grasp the wings 74a and 74b, whereas a thumb grasps a rear portion of the housing 12. By squeezing the thumb and fingers together, handle 26 (and thus tabs 28a and 28b) is refracted. This process is used once to retract the cannula 18 and once to retract the stylet 16. In the illustrated embodiment, tab 28a is positioned on the same side of the housing 12 as buttons 32 and 34, providing a useful interface where the practitioner can easily slide the thumb from the rear of the housing to the top of the housing to actuate buttons 32 and 34. To this end, practitioners generally desire to actuate buttons 32 and 34 when in a vertical orientation so that a visual indication of the buttons is provided as well as an easier orientation for actuation of the buttons. Once loaded, handle 26 is removed from housing 12, reducing the profile of device 10 so that the practitioner can approach tissue of interest from a larger range of angles.

As illustrated in FIG. 5, biopsy device 10 is in the loading configuration, where handle 26 is coupled to housing 12, creating a large overall profile P of the device 10, which is illustrated as a height dimension. As a result, if one were to attempt a biopsy procedure in the loading configuration (where buttons 32 and 34 are in a vertical orientation), a large angle α (e.g., greater than 20°) of approach for device 10 relative to tissue T is created due to interference between handle 26 and tissue T. As such, a sample S of tissue removed from a mass M is smaller than a desired amount of mass M obtained and may not provide reliable indication of outer margins of the mass M and/or the extent of mass M.

Figure 6:
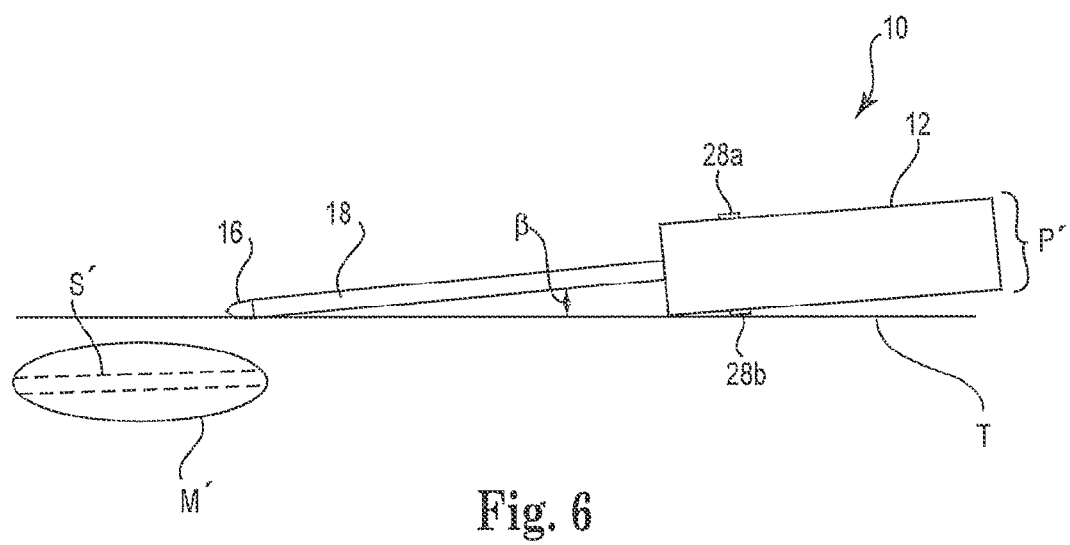
FIG. 6 is a schematic view of the biopsy device in a delivery configuration in relation to a target tissue site.

In contrast, as illustrated in FIG. 6, in the delivery configuration, handle 26 has been removed, creating a reduced profile P' and a smaller angle β (e.g., approximately 3-5°) of approach. In FIG. 6, sample S' obtains more tissue of mass M' as compared to sample S due to the angle of approach β. As such, the biopsy procedure, when conducted in the delivery configuration, is more effective in obtaining samples of a mass. The delivery configuration is also useful in biopsy procedures where multiple samples are obtained from a single tissue site. In such a situation, the practitioner rotates the device 10 to different positions (e.g., with respect to a clock orientation) about the tissue site. In particular, the orientation of indentation 40 is altered (i.e., rotated about an axis coaxial with cannula 18) so as to face in different directions relative to a mass. Without interference from handle 26, each approach to the tissue site can be achieved in a consistent manner so as to obtain a more complete set of samples for a particular site.

It is worth noting that other embodiments are envisioned for reducing the profile of device 10, yet still allow convenient loading of the device 10. For example, in one embodiment, handle 26 can be permanently coupled to tabs 28a and 28b, wherein hinges 11 (or another mechanism) are provided to fold wings 74a and 74b so as to enter slots 30a and 30b (or be proximate thereto), after loading device 10. Thus, wings 74a and 74b will not interfere with tissue during a delivery configuration, yet reduce the profile of the device 10 upon folding. Moreover, handle 26 remains coupled to the housing 12 during operation of the device 10.

The components of the device 10 can be made and assembled using various conventional materials, techniques and equipment known in the art. In general, the components of the device can be made from rigid materials such as plastics and metals and metallic alloys. In one embodiment, the housing and some of the components of the control device for the biopsy needle assembly can be composed of plastic, whereas the cannula components and stylet can be composed of metals such as stainless steel. Components such as the longitudinal adjusting element, for example, can be composed of either plastic or metal.

In a further embodiment, device 10 can be provided with a kit for performing biopsy procedures. In addition to the biopsy device as described herein, the kit can include instruments and equipment which are associated with biopsy procedures. Examples of such instruments and equipment include, but are not limited to, syringes (and needles), local anesthetics, microscope slides, scalpels, rulers, drapes, swabs, vials, labels, storage solutions, forceps, sponges, bandages, cups and wraps. Packaging or containers which house the biopsy device along with the other components used in the biopsy kit can also be included.

In yet a further embodiment, the kit can be provided in a sterilized pouch, which provides device 10 in a sterilized field for conducting biopsy procedures. To preserve sterility of handle 26, a lanyard can be provided to attached the handle 26 to the device 10. As such, when handle 26 is removed from the housing 12, the handle 26 remains coupled to device 10 so as to prevent handle 26 from contacting objects that are not sterilized. Alternatively, a clinician conducting the biopsy procedures can position the handle 26 on an inside of the sterilized pouch after using handle 26 to load device 10, thus preventing contact of the handle 26 with objects that may not be sterilized. In another alternative, the sterilized pouch can include a sterilized cloth or wrap that the clinician can use to place on a flat surface such as a table. The clinician can then place handle 26 on the cloth or wrap so as to preserve sterility of the handle 26 so as to obtain multiple samples while handle 26 remains sterilized.

Figure 7:
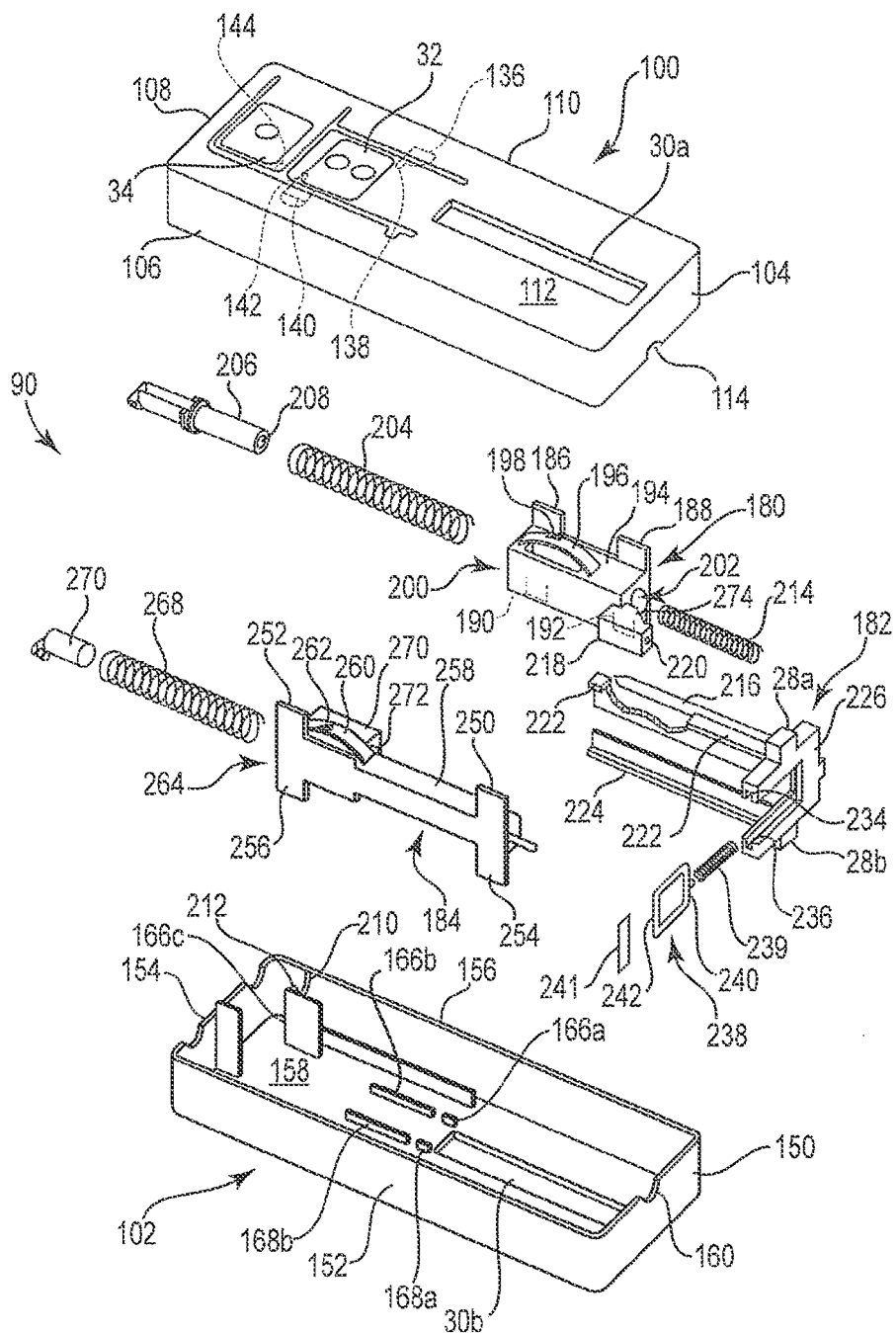
FIG. 7 is an exploded perspective view of a control device and a housing of the biopsy device.

FIGS. 7-11 illustrate components of control device 90 within the housing 12, which operates to control actuation of the stylet 16 and cannula 18 to obtain tissue samples. Housing 12 includes two semi-shells 100 and 102. As maintained above, housing 12 (and the shells 100 and 102) can be integrally formed with body 15 or provided separately. In the embodiment of FIGS. 7-11, body 15 is formed separately. Upper shell 100 seen in FIGS. 7-9 is made up of a front wall 104, a side wall 106, a back wall 108, a side wall 110 and an upper wall 112, where front wall 104 includes a semi-hole 114 for the passage of a biopsy needle assembly (i.e., stylet 16 and cannula 18). Upper wall 112 includes slot 30a, button 32 bending in a longitudinal plane and button 34 bending in a transversal plane. An inner surface of upper wall 112, as shown in FIGS. 8 and 9, includes a first longitudinal elevation 122 which configures a longitudinal sliding channel 124 with wall 110, a couple of elevations 126 and 128 which configure a central longitudinal sliding channel 130 between them, a second elevation 132 which configures a longitudinal sliding channel 134 with side wall 106, a holding tooth 136, a pushing tooth 138, a holding tooth 140, a pushing tooth 142 and a pushing tooth 144. The pushing teeth 138 and 142 are carried by button 32, and the tooth 144 is carried by button 34, so as to be mobile downwards if a force is applied inwards on outer buttons 32 or 34.

The lower shell 102 (FIGS. 7 and 10-11) is formed with front wall 150, a side wall 152, a back wall 154, a side wall 156 and a lower wall 158, where front wall 150 presents a half hole 160 for the passage of a needle assembly (i.e., stylet 16 and cannula 18). The lower wall 158 includes a longitudinal elevation 162 which configures a longitudinal sliding channel 164 with wall 156, a double series 166a, 166b, 166c and 168a, 168b, of elevations aligned lengthwise which configure a central sliding channel 170 between them, an elevation 172 which configures a longitudinal sliding channel 174 with wall 152 and, in the center, a passing slot 30b, corresponding to slot 30a on upper shell 100.

With reference to FIG. 7, inside the shells 100 and 102, a cannula slider 180, a loader slider 182 and a stylet slider 184 slide lengthwise. The cannula slider 180 is formed for guided longitudinal sliding, with a couple of upper flaps 186 and 188 suitable for sliding in the longitudinal channel 124 of upper shell 100 and, below, a couple of flaps 190 and 192 suitable for sliding in the longitudinal channel 164 of lower shell 102. The four mentioned flaps 186, 188, 190 and 192 are carried by a main body 194 having on its top an elastic bridge 196 equipped with a holding mobile tooth 198 and inside the body 194 a back housing 200 and an additional front housing 202 are provided. Housing 200 receives a spring 204 which has its opposite end triggered on a pin 206 equipped with a longitudinal hole 208. The pin 206 is carried by back wall 154 of shell 102 and by two shoulders 210 and 212. The housing 202 houses a spring 214 and spring guide rod 216 with a diameter which is smaller than that of the hole 208 so as to pass through the interspace between the two housings 200 and 202 for the reasons described and explained hereinafter. A front part of the cannula slider 180 includes a head 218 extending transversely and having coaxially a hole 220 suitable for carrying cannula 18.

The loader slider 182 slides lengthwise and is guided in the upper sliding channel 130 of the shell 100 and in the lower guiding channel 170 of shell 102. The loader slider 182 is provided with a fork central body with tines 222 and 224, a head 226, spring guiding rod 216 on which spring 214 is triggered, maintaining tabs 28a and 28b suitable for coupling with the handle 26 and sliding inside respective slots 30a and 30b of shells 100 and 102.

Head 226 presents a "U" reversed configuration in which two transversal guides 234 and 236 are made and suitable for carrying a square element 238 sliding transversely and loaded elastically by a spring 239 against a limit stop 241, inhibiting its exit from head 226. The square 238, when inserted into guides 234 and 236, has two vertical sides (serving as strikers) 240 and 242 mobile transversely and respectively destined to selectively meet front faces of cannula slider 180 and stylet slider 184 as better described hereinafter.

The stylet slider 184 is formed with a couple of upper flaps 250 and 252 suitable for sliding in the longitudinal channel 134 and, below, a couple of flaps 254 and 256 suitable for sliding in the lower longitudinal channel 174. The mentioned flaps are carried by a main body 258 having on its top an elastic bridge 260 equipped with a mobile tooth 262 and a housing 264 inside. The housing 264 carries a spring 268 which has its opposed end triggered on a pin 270 carried by the wall 154 of lower shell 102. The back part of the stylet slider 184 includes a head 270, extending transversely from body 258, which includes a hole 272 for coupling with the stylet 16.

Device 10 is generally operable in three positions, namely an idle position, a partially retracted position and a fully refracted position. In the idle position, sliders 180, 182 and 184 are pressed on front walls 104 and 150 by the respective springs 204, 214 and 268.

The square 238, sliding transversely to the y-axis, is loaded by spring 239 which presses it on the limit stop 241 within head 226 so that side 242 is aligned lengthwise to meet an inclined plane 274 of cannula slider 180 and side 240 is aligned lengthwise to meet a front part of stylet slider 184.

In the loading configuration, where handle 26 is coupled to tabs 28a and 28b, the operator acts to move the loader slider 182 backwards by grasping the handle 26. As the loader slider 182 starts moving towards the back part to begin winding or loading operations, striker 242 interferes with an inclined plane 274 of head 218, thus entailing a displacement of the relative square 238 on the left, so that striker 240 does not interfere with a front part of stylet slider 184.

During this loading operation, the loader slider 182 has been pulled backwards and it has dragged cannula slider 180 with itself. The cannula slider 180, moving backwards, has compressed spring 204 and mobile holding tooth 198, carried by elastic bridge 196, hooks with fixed holding tooth 136 carried by shell 100. With reference to this hooking, mobile holding tooth 198 clutches with fixed tooth 136 and that bridge 196 includes an upper portion, extending lengthwise and arranged transversely at a side of the tooth 198, which is aligned vertically with pushing tooth 138 carried by button 32, so that, by pressing the button 32, pushing tooth 138 presses on bridge 196 and as it is pressed down it is lowered with subsequent release of teeth 136 and 198.

After this loading operation, loader slider 182 after loading cannula slider 180 as mentioned above, returns to the former position by pushing spring 214 while square 238 is loaded by spring 239 against limit stop 241.

To load the stylet 16, loader slider 182 is pulled again towards the back, dragging stylet slider 184 with itself. In this respect please note that since cannula slider 180 is positioned towards the back, square 238 is not subject to transversal displacements by inclined plane 274.

Stylet slider 184, moving backwards, has compressed spring 268 and mobile holding tooth 262, carried by elastic bridge 260, hooks with fixed holding tooth 140 carried by shell 100. With reference to that hooking, please note that mobile holding tooth 262 clutches with fixed tooth 140 and that bridge 160 includes an upper portion, extending lengthwise and arranged transversely at a side of tooth 262, which is aligned vertically with pushing tooth 142 carried by button 34, so that, by pressing said button 34, presses on tooth 142 pushes bridge 160 and as it is pressed down it is lowered with subsequent release of teeth 262 and 140.

After winding stylet slider 184, loader slider 182 returns to its front position by pushing spring 214.

After executing the above-mentioned winding operations, the stylet slider 184 is loaded and held in position through hooking of teeth 140-262 while cannula slider 180 is loaded and held in position through hooking of teeth 136-198. Furthermore, button 32 has two pushing teeth 138 and 142 where pushing tooth 138 can press elastic bridge 196 of cannula slider 180 in order to release it and pushing tooth 140 can press elastic bridge 260 of stylet slider 184 to release it.

With reference to the type of removal to be performed, the operator must wind the appliance as described above first, remove the handle 26 from housing 12, and then insert needle (i.e., stylet 16 and cannula 18) in the tissue and position its free point in the area destined to removal.

At this point the operator may opt for two different types of removal, a first type where the stylet 16 and the cannula 18 are advanced in successive quick sequence by a single control, or a second type of removal where stylet 16 is advanced by a first control and cannula 18 by a second control.

With reference to first type of removal, the operator, applying a strength directed from outside to inside on button 32, moves pushing teeth 138 and 142 downwards with different movements, where tooth 138 during bending phase executes downwards movements which are greater with respect to tooth 142.

More particularly, flexure of button 32 entails first stylet slider 184 release through pushing tooth 142 pressure on bridge 260 which involves mobile holding tooth 262 to be released from fixed holding tooth 140 with subsequent advancement of stylet slider 184 by pre-wound spring 268. Then, due to further flexure of button 32, it entails mobile holding tooth 198 release from fixed holding tooth 136 with subsequent advancement of cannula slider 180 by pre-wound spring 204.

In such a manner, advancement of stylet 16 and cannula 18 is obtained in quick sequence as required for first type of removal, and in case stylet 16 and therefore the relative slider 184 because of a particularly hard tissue do not reach advancement limit stop, cannula 18 executes its cutting stroke all the same since the release of the holding means 198-136 is independent from the system relative to stylet slider 184.

With reference to the second type of removal, the operator, applying a first control through a first strength directed from outside to inside on the button 34, moves bridge 261 downwards through pushing tooth 144, thus entailing the release of holding tooth 262 from holding tooth 140 with subsequent advancement of stylet slider 184 by pre-wound spring 268. Then, after examining the correct arrangement of needle tip 42 of stylet 16 by magnetic resonance, computed axial tomography or other systems, the second control is operated through the application of a strength on button 32 by releasing cannula slider 180 as aforementioned.

In such a manner, advancement of cannula 18 is obtained also in case slider 184, because of a particularly hard tissue found at stylet point 16, does not reach an advancement limit stop, since the release of the holding means 198-136 of cannula slider 180 are not associated with stylet slider 184.

Although the present disclosure has been described with reference to preferred embodiments, workers skilled in the art will recognize that changes can be made in form and detail without departing from the spirit and scope of the present disclosure.

What is claimed is:

1. A biopsy device, comprising:
   a housing maintaining a stylet and a cannula;
   a control device operable to actuate the stylet and the cannula with respect to the housing, the control device including tabs extending through slots in the housing; and
   a removable handle configured to facilitate arming of coupleable to the control device so as to load the stylet and the cannula by overcoming a biasing force imparted by a biasing member,
   wherein the handle is configured to modify the device from a loading configuration to a delivery configuration such that the device has a reduced profile for obtaining a tissue sample, and
   wherein the handle is adapted to engage the tabs in the loading configuration.

2. The biopsy device of claim 1 wherein the handle is configured to be foldable with respect to the housing.

3. The biopsy device of claim 1, wherein the handle includes a body defining an inner perimeter configured to be positioned around the housing.

4. The biopsy device of claim 3, wherein the handle further includes first and second wings extending from the body, the wings configured to be grasped by a user.

5. The biopsy device of claim 1, further comprising:
   a cannula insertion guide co-axially aligned with and accommodating the stylet and the cannula;
   a longitudinal adjusting element coupled to the housing,
   wherein the longitudinal adjusting element is adapted to co-axially adjust the position of the cannula insertion guide relative to the stylet and the cannula.

6. The biopsy device of claim 1, wherein the housing includes a first button of the control device configured to sequentially actuate the stylet and the cannula and a second button configured to independently actuate the stylet.

7. The biopsy device of claim 1, wherein the handle includes foldable wings extending from the housing, the wings being folded relative to the housing to modify the device to the delivery configuration.

8. A biopsy device, comprising:
a housing maintaining a stylet and a cannula;
a control device operable to actuate the stylet and the cannula with respect to the housing; and
a handle comprising a plurality of wings each foldable about a hinge and configured to facilitate arming of the control device so as to load the stylet and the cannula by overcoming a biasing force imparted by a biasing member,
wherein the handle is configured to modify the device from a loading configuration to a delivery configuration such that the device has a reduced profile for obtaining a tissue sample,
wherein the wings are configured to be grasped by a user.

9. The biopsy device of claim 8 wherein the wings are configured to be foldable with respect to the housing.

10. The biopsy device of claim 8, wherein the control device includes tabs extending through slots in the housing, the handle adapted to engage the tabs in the loading configuration.

11. The biopsy device of claim 8, wherein the handle includes a body defining an inner perimeter configured to be positioned around the housing.

12. The biopsy device of claim 8, further comprising:
a cannula insertion guide co-axially aligned with and accommodating the stylet and the cannula;
a longitudinal adjusting element coupled to the housing,
wherein the longitudinal adjusting element is adapted to co-axially adjust the position of the cannula insertion guide relative to the stylet and the cannula.

13. The biopsy device of claim 8, wherein the housing includes a first button of the control device configured to sequentially actuate the stylet and the cannula and a second button configured to independently actuate the stylet.

14. The biopsy device of claim 8, wherein the wings extend from the housing, the wings being folded relative to the housing to modify the device to the delivery configuration.

15. The biopsy device of claim 8, wherein the handle is configured to modify the device from a loading configuration to a delivery configuration such that the device has a reduced profile around the housing for obtaining a tissue sample.

16. The biopsy device of claim 8, wherein the plurality of wings comprises a first wing and a second wing, the first and second wing extending from opposing sides of the housing.

17. A biopsy device, comprising:
a housing maintaining a stylet and a cannula, the housing including upper and lower slots;
a control device operable to actuate the stylet and the cannula, the control device including upper and lower tabs extending through the upper and lower slots of the housing, respectively; and
a removable handle including an inner perimeter shaped to be positioned around the housing, a body configured to engage the upper and lower tabs of the control device, and first and second wings each foldable about a hinge and extending from the body, the first and second wings shaped to be grasped by a user to facilitate arming of the control device to load the stylet and cannula by overcoming a biasing force imparted by a biasing member when the body engages the upper and lower tabs of the control device.

18. The biopsy device of claim 17, further comprising:
a cannula insertion guide co-axially aligned with and accommodating the stylet and the cannula;
a longitudinal adjusting element coupled to the housing,
wherein the longitudinal adjusting element is adapted to co-axially adjust the position of the cannula insertion guide relative to the stylet and the cannula.

19. The biopsy device of claim 17, wherein the housing includes a first button of the control device configured to sequentially actuate the stylet and the cannula and a second button configured to independently actuate the stylet.

20. The biopsy device of claim 19, wherein the first button and the second button are positioned on a side of the housing maintaining one of the upper and lower slots.

* * * * *